United States Patent [19]

Ma et al.

[11] Patent Number: 6,146,892
[45] Date of Patent: Nov. 14, 2000

[54] FIBRILLAR MATRICES

[75] Inventors: Peter X. Ma; Ruiyun Zhang, both of Ann Arbor, Mich.

[73] Assignee: The Regents of the University of Michigan, Ann Arbor, Mich.

[21] Appl. No.: 09/162,071

[22] Filed: Sep. 28, 1998

[51] Int. Cl.$^7$ ....................................................... A61F 2/00
[52] U.S. Cl. .............................. 435/399; 521/52; 521/82; 521/87; 521/88; 521/90; 521/94; 521/97; 521/913; 521/916; 435/363; 435/396; 435/400; 435/402; 435/246; 264/81; 264/45.6; 264/45.8; 264/45.9; 264/46.4; 264/46.6; 264/46.8; 264/48; 264/53
[58] Field of Search ................................. 521/52, 82, 87, 521/88, 90, 94, 97, 913, 916; 435/246, 393, 396, 399, 400, 402; 264/41, 45.6, 45.8, 45.9, 46.4, 46.6, 46.8, 48, 53

[56] References Cited

U.S. PATENT DOCUMENTS

| | | | |
|---|---|---|---|
| 3,812,224 | 5/1974 | Smith et al. | 264/28 |
| 5,686,091 | 11/1997 | Leong et al. | 424/426 |

OTHER PUBLICATIONS

Ma, P. et al., "Degradation, Structure and Properties of Fibrous Nonwoven Poly(Glycolic Acid) Scaffolds for Tissue Engineering," in *Polymers in Medicine and Pharmacy*, A.G. Mikos, et al., Editors 1995, MRS: Pittsburgh 394:99–104.
Ma, P. et al., "Development of biomechanical properties and morphogenesis of in vitro tissue engineered cartilage," *J. Biomed Mater Res*, 29(12):1587–1595 (1995).
Ma, P. et al., "Fabrication of Biodegradable Polymer Foams for Cell Transplantation and Tissue Engineering," *Tissue Engineering*, M.Yarmush and J. Morgan, Editors. 1998, Humana Press Inc.: Totowa, NJ.
Shinoka, T. et al., "Tissue–engineered heart valves. Autologous valve leaflet replacement study in a lamb model," *Circulation* 94(9 Suppl):II–164–168 (1996).
Kim, T. et al., "Enhanced Survival of Transgenic Hepatocytes Expressing Hepatocyte Growth Factor in Hepatocyte Tissue Engineering," *Transplant Proc.*, 29(1–2):858–860 (1997).
Ma, P. et al., "Biodegradable woven/nonwoven composite scaffolds for pulmonary artery engineering in an juvenile lamb model," *Transaction of the Society for Biomaterials* p. 295 (1997).
Cao, Y. et al., "Tissue Engineering of Tendon," in *Polymers in Medicine and Pharmacy*, A.G. Mikos, et al., Editors 1995, MRS: Pittsburgh 39:83–89.
Shinoka, T. et al., "Tissue–Engineered Heart Valve Leaflets. Does Cell Origin Affect Outcome?," *Circulation* 96(9 Suppl):II–102–107 (1997).
Zund, G. et al., "The in vitro construction of a tissue engineered bioprosthetic heart valve," *Eur J Cardiothorac Surg* 11(3):493–497 (1997).
Breur, C. et al., "Tissue Engineering Lamb Heart Valve Leaflets," *Biotechnology and Bioengineering* 50:562–567 (1996).
Shinoka, T. et al., "Tissue Engineering Heart Valves: Valve Leaflet Replacement Study in a Lamb Model," *Annals of Thoracic Surgery* 60(6 Suppl):S513–516 (1995).
Shinoka, T. et al., "Creation of Viable Pulmonary Artery Autografts through Tissue Engineering," *J. Thoracic & Cardiovascular Surgery* 115(3):536–545 (1998).
Rehman, I. et al., "Characterization of hydroxyapatite and carbonated apatite by photo acoustic FTIR spectroscopy,"; *J. Materials Science: Materials in Medicine* 8:1–4 (1997).
Whinnery, L. et al., "Engineering the Macrostructure of Thermally Induced Phase Separated Polysilane Foamsm," *J. Polymer Science: Part A: Polymer Chemisty* 34:1623–1627 (1996).
Akao, M. et al., "Mechanical properties of sintered hydroxyapatite for prosthetic application," *J. Materials Science* 16:809–812 (1981).
Akao, M. et al., "In vitro mineralization in bovine tooth germ cell cultured with sintered hydroxyapatite," *J. Materials Science: Materials in Medicine* 4:569–574 (1993).
Verheyen, C. et al., "Evaluation of hydroxylapatite/poly (L–lactide) composites: physico–chemical properties," *J. Materials Science: Materials in Medicine* 4:58–65 (1993).
Lo, H. et al., "Fabrication of Controlled Release Biodegradable Foams by Phase Separation," *Tissue Engineering* 1(1):15–28 (1995).
Schugens, C. et al., "Polyactide macroporous biodegradable implants for cell transplantation. II. Preparation of polylactide foams by liquid–liquid phase separation," *J. Biomedical Materials Research* 30:449–461 (1996).
Kokubo, T. et al., "Solutions able to reproduce in vivo surface–structure changes in bioactive glass–ceramic A–W$^3$," *J. Biomedical Materials Research* 24:721–734 (1990).
Kitsugi, T. et al., "Bone bonding behavior of MgO–CaO–SiO$_2$–P$_2$O$_5$–CaF$_2$ glass (mother glass of A–W–glass–ceramics)," *J. Biomedical Materials Research* 23:631–348 (1989).
Langer, R. et al., "Tissue Engineering," *Science* 260:920–926 (1993).
Mikos, A. et al., "Preparation and characterization of poly(L–lactic acid) foams," *Polymer* 35(5):1068–1077 (1994).
Nerem, R. et al., "Tissue Engineering: From Biology to Biological Substitutes," *Tissue Engineering* 1(1):3–13 (1995).
Flahiff, C. et al., "Analysis of a biodegradable composite for bone healing," *J. Biomedical Materials Research* 32:419–424 (1996).
Puleo, D. et al., "Osteoblast responses to orthopedic implant materials in vitro," *J. Biomedical Materials Research* 25:711–723 (1991).

*Primary Examiner*—Frederick Krass
*Attorney, Agent, or Firm*—Medlen & Caroll, LLP

[57] ABSTRACT

Methods and compositions are described that provide three-dimensional fibrillar matrices useful as, among other things, structural prosthetics and scaffolds for cells. The porous fibrillar matrices of the present invention have desirable mechanical properties suitable to a variety of applications, including platforms for in vitro cell cultivation, implants for tissue and organ engineering, implants as tendon and facia prosthetics, and product packaging.

63 Claims, 14 Drawing Sheets

(a)
 (b)
 (c)
 (d)

(a) (b) (c) (d)

(a)  (b)

(a)

(b)

(c)

(d)

FIBRILLAR MATRICES

FIELD OF THE INVENTION

The present invention relates to methods of fabrication for fibrillar matrices as well as the resulting fibrillar matrices as compositions suitable as a scaffold for cellular infiltration and ingrowth, the cultivation of cells within said matrices for the fabrication and repair of tissues and organs, and as biocompatible synthetic prosthesis. In addition, said fibrillar matrices have applications as biodegradable packaging materials.

BACKGROUND

Transplantation is a life-saving therapy but is seriously limited by the scarcity of donor organs. In contrast to native tissue and organ transplantation from a nonautologous donor, tissues and organs generated through tissue engineering provide a more abundant alternative source for highly sought after biological materials. Scaffolding plays a pivotal role in the engineering of new tissues and organs by providing a support and a framework within which blood vessels, lymphatic vessels, and nerves may course.

Collagen is a natural extracellular matrix component of many tissues such as bone, skin, tendon, ligament, and other connective tissues. Collagen's fibrillar structure is important for cell attachment, proliferation, and differentiation.

Collagen fiber bundles vary in diameter from 50 to 500 nm. As a natural extracellular matrix component, collagen facilitates cellular recognition. Cellular recognition is advantageous for promoting cell attachment and infiltration. Importantly, however, cellular recognition may also precipitate a deleterious inflammatory or pathological immunogenic response. Native collagen is also undesirable as an implant or prosthesis due to the inherent batch to batch variability in mechanical specifications and degradability of said native collagen derived from biological sources.

In contrast, aliphatic polyesters such as (but not limited to) poly(lactide), poly(glycolide) and their copolymers are biodegradable, biocompatible (e.g., non-immunogenic), and among the few synthetic polymers approved by FDA for some human clinical applications. The prior art presents three-dimensional porous structures fabricated from synthetic aliphatic polyesters employed for cell attachment, growth, and tissue regeneration. However, these porous scaffolds (in the prior art) do not approximate the fibrillar morphology of a native collagen extracellular matrix.

In an attempt to approximate a native collagen extracellular matrix, the prior art has applied textile technology to produce nonwoven fabrics from aliphatic polyesters. These nonwoven fabrics, however, require the expensive and laborious steps of fiber extrusion, drawing, crimping, cutting into stable fibers, carding, needling, heat platen pressing, degreasing, and punching. Furthermore, said textile produced nonwoven fabrics are associated with structural parameters (as compared with native collagenous matrices) that do not favor cell attachment (e.g., large fiber diameter and low surface to volume ratios).

What is needed, therefore, is a biocompatible synthetic fibrillar matrix (readily fashioned into a desired shape) that reproduces the form and function of native collagenous extracellular matrices.

SUMMARY OF THE INVENTION

The present invention relates to methods of fabrication for fibrillar matrices as well as the resulting fibrillar matrices as compositions suitable as a scaffold for cellular infiltration and ingrowth, the cultivation of cells within said matrices for the fabrication and repair of tissues and organs, and as biocompatible synthetic prostheses. In one embodiment, the present invention contemplates a method wherein a synthetic fibrillar matrix of a desired fiber diameter, porosity, and unit length is used to approximate the morphology of native collagenous extracellular matrices. In another embodiment, the present invention contemplates a method wherein a fibrillar matrix of an implantable material, comprising a desired fiber diameter, porosity, and unit length is used as a scaffold facilitating the infiltration of cells in vivo. In another embodiment, the present invention contemplates a fibrillar matrix of an implantable composite material, comprising a desired fiber diameter, porosity, and unit length as a composition providing a biocompatible implantable prosthetics. In addition, said fibrillar matrix has applications as a packaging material.

In one embodiment, the present invention contemplates a method comprising: a) providing: i) a polymer source, ii) a solvent; b) mixing said polymer with said solvent at a temperature range between 20–100° C., more preferably between 50–65° C., and most preferably at 60° C. to create a homogenous polymer solution; c) casting said homogenous polymer solution into a desired form at a temperature range between 20–100° C., more preferably between 50–65° C., and most preferably at 50° C.; d) cooling said cast homogenous polymer solution to a given gelation temperature wherein said temperature favors the fabrication, that is to say the spatial orientation, of a three-dimensional fibrillar matrix, said temperature comprising a range between −195.8° C. and 23° C. and more preferably between −18° C. and 8° C.; e) maintaining said cast homogenous polymer solution at a given gelation temperature under conditions wherein said three-dimensional fibrillar network is preserved, said fibrillar network comprising fibers with diameters in a range between 50 to 500 nm, and most preferably with an average diameter between 160–170 nm; f) hydrating said gelled polymer such that said hydrated polymer is solvent free; g) freezing said hydrated solvent free gelled polymer; and h) treating said frozen gelled hydrated solvent free polymer under conditions whereby a substantially desiccated matrix is created having a porosity greater than 80%. While the above-named components can be formulated in an alternative order, the above referenced reaction sequence has been found to produce the best results.

In another embodiment, the present invention contemplates a method comprising: a) providing: i) a polymer source, ii) a solvent; b) mixing said polymer with said solvent at a temperature range between 20–100° C., more preferably between 50–65° C., and most preferably at 60° C. to create a homogenous polymer solution; c) casting said homogenous polymer solution into a desired form at a temperature range between 20–100° C., more preferably between 50–65° C., and most preferably at 50° C.; d) cooling said cast homogenous polymer solution to a given gelation temperature wherein said temperature favors the fabrication, that is to say the structural orientation, of a three-dimensional fibrillar matrix, said temperature comprising a range between −195.8° C. and 23° C. and more preferably between −18° C. and 8° C.; e) maintaining said cast homogenous polymer solution at a given gelation temperature under conditions wherein said three-dimensional fibrillar network is preserved, said fibrillar network comprising fibers with diameters in a range between 50 to 500 nm, and most preferably with an average diameter between 160–170 nm; f) freezing said gelled polymer; and g) treating said frozen gelled polymer under conditions whereby a substantially desiccated matrix is created having a porosity greater than 80%. While the above-named components can be formulated in an alternative order, the above referenced reaction sequence has been found to produce the best results.

It is not intended that the present invention be limited to the above-described reagents. While the basic components are described above, other components can be added to the basic components, creating variations in the final structures (and thereby conferring different functions). Examples of such other components include, but are not limited to, biologically functional substances (such as proteins, drugs and growth factors) and pore-forming components (such as salt, sugar, water soluble waxes or other water-soluble substances). The present invention contemplates adding such additional components such as pore-forming components to the polymer solution to produce additional pores when leached in water.

In another embodiment the instant invention contemplates a composition, said composition comprising a three-dimensional aliphatic polyester fibrillar matrix, wherein said fibrillar matrix comprises fibers having diameters in a range between 50 to 500 nm, and most preferably with an average diameter between 160–170 nm, and said fibrillar matrix has a porosity of greater 80%.

It is not intended that the matrix recited in the instant invention be limited to a specific morphology. In one example said matrix may be fibrillar. In another example, said matrix may be a foam.

It is not intended the present invention be limited to a particular polymer or polymer source. The present invention contemplates homopolymers, copolymers and/or a mixture of polymers. In one embodiment, the polymer source is poly(L-lactic acid) (PLLA) with an inherent viscosity of approximately 1.6. In another embodiment, the polymer is poly(D,L-lactic acid-co-glycolic acid (PLGA) with an inherent viscosity of 0.5–0.6. In another embodiment, the polymer is Poly(D,L-lactic acid) (PDLLA) with a molecular weight of approximately 103,000. Said polymers are commercially available and may be purchased from Boehringer Ingelheim (Ingelheim, Germany) and/or Sigma Chemical Co. (St. Louis, Mo.). Additionally, these polymers are used without further purification.

It is also not intended that the present invention be limited to a specific solvent. In one embodiment the solvent is dioxane (D). In another embodiment the solvent is a solution of dioxane and water (D/W). In another embodiment the solvent is tetrahydrofuran (THF). In another embodiment the solvent is N,N-dimethylformamide (DMF). In another embodiment the solvent is pyridine. In another embodiment the solvent is methanol. In another embodiment the solvent is acetone.

The present invention also contemplates the use of a composition. Moreover, the present invention contemplates using a synthetic fibrillar matrix that approximates the morphology of a native collagenous extracellular matrix in combination with other components, such as cells. Where cells are used, it is not intended that the present invention be limited to a specific cell type (e.g. one cell type infiltrating a matrix). A variety of cell types (including solutions of different cells) are contemplated. In one embodiment, the cells are osteoblasts. In another embodiment, the cells are fibroblasts. In another embodiment the cells are epithelial. In another embodiment, the cells secrete a medically useful compound (e.g., hormone, cytokine, etc.). Such cells may be (but need not be) cells that have been manipulated by recombinant means to secrete such compounds.

The present invention contemplates methods wherein cells are added and grown in and on the matrix, as well as methods wherein the matrix is implanted (both with and without cells).

The present invention also contemplates methods wherein some of the fibrillar matrices that approximate the morphology of a native collagenous extracellular matrix biodegrade, in vivo and in vitro, subsequent to the confluent growth of cells in and on the matrix. The present invention also contemplates methods wherein some of the collagen like fibrillar matrices are not biodegradable. While it is not intended the instant invention be limited to a particular example, said non-biodegradable fibrillar matrices are fashioned into synthetic tendons and facia (e.g., Achilles tendon and plantar facia).

As noted above, the fibrillar matrix of the present invention may also be applied as a packaging material.

DEFINITIONS

To facilitate understanding of the invention, a number of terms are defined below.

A "Fibrillar matrix" refers to a three dimensional support for cells, comprising an array of strand-like or thread like elements, which divide free space into partially enclosed domains which remain in fluidic communication with adjacent domains.

"Biodegradable" refers to a material capable of being broken down into readily metabolized compounds by the action of living beings such as cells in vitro or in vivo.

As used herein, the term "implant" and "implanting" and the like indicates placement on, in, or through a patient's body (including placement in body cavities) in the course of medical treatment, e.g., for a disease, impairment or injury. Implants include, but are not limited to, implants for wound care, and drug delivery.

"Solvent free" refers to a polymer matrix wherein the interstices of said matrix are substantially free from residual solvent such that said matrix reaches a constant mass upon sublimation. By "substantially free" it is meant that, with normal detection means (such as detection by changes in mass), no solvent is detected. While it is believed that the methods of the present invention yield a matrix that is completely free of solvent, it is possible that some solvent remains detectable in extremely small amounts by extreme detection methods (e.g., detection methods with extremely high resolution).

"Quenching" refers to the cooling rate of a solution.

"Surface/volume ratio" refers to the ratio of surface area within a matrix sample to the polymer skeleton volume of the same matrix sample.

"Unit length" is the linear distance of a fiber length between two conjunctions of fiber.

"Native Collagen Extracellular Matrix" refers to a three dimensional support for cells, comprising a triple-stranded helical molecule rich in proline and hydroxyproline, which divide free space into partially enclosed domains which remain in fluidic communication with adjacent domains.

"Gelation Time" refers to the elapsed time from the time point when a polymer/solvent solution sample is set to a target gelling temperature to the time point when said polymer/solvent sample (held at said target gelling temperature) does not flow down an incline plane.

"Structural prosthetics" refers to load bearing synthetic tissue including but not limited to synthetic tendons and facia and portions thereof.

"Substantially desiccated" refers to a material sample that has a water content of 10% or less, and more preferably 5% or less, and still more preferably 1% or less.

"Resorbable" refers to a synthetic or native materials which may be broken down into less complex constituent parts by physiological processes.

"Foam" refers to a solid within which is disposed a plurality partially enclosed domains which remain in fluidic communication with adjacent domains.

"Salt" refers to any of a class of chemical compounds formed by neutralization of an acid by a base. While it is not intended that the present invention be limited to any particular salt, examples include NaCl, KCl, $MgCl_2$, and $CaCl_2$.

"Sugars" refers to polyhydroxy aldehydes or ketones and their derivatives.

"Water soluble waxes" refers to the water soluble subset of a group of substances composed of hydrocarbons, alcohols, fatty acids, and esters that are solid at room temperature.

(A) Maintained at room temperature for 2 hours, and then quenched to −18° C.;

(B) Maintained at room temperature for 12 hours, and then quenched to −18° C.;

(C) Maintained at room temperature for 24 hours, and then quenched to −18° C.; and (D) Quenched to −18° C. for 10 minutes, and then maintained at room temperature for one week.

Figure 9:
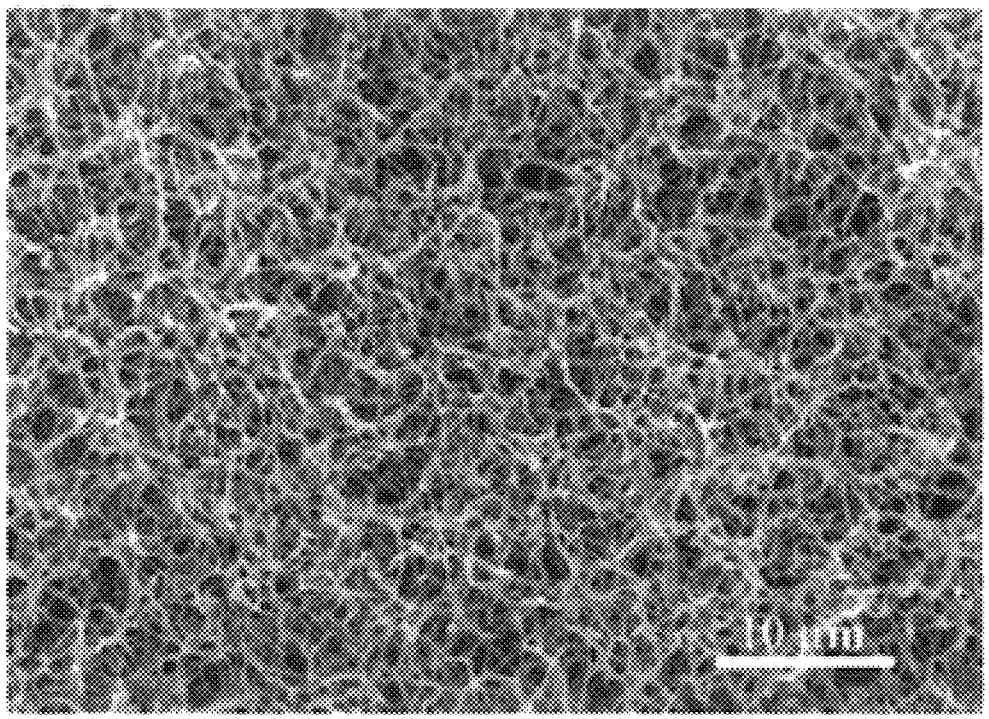

FIG. 9 presents a Scanning Electron Micrograph (SEM), at a magnification of 2,000×, of a PLLA fibrillar matrix prepared from a 5.0% (wt/v) PLLA/THF/methanol (THF/methanol=80/20) solution at a gelation temperature of liquid nitrogen.

Figure 10:
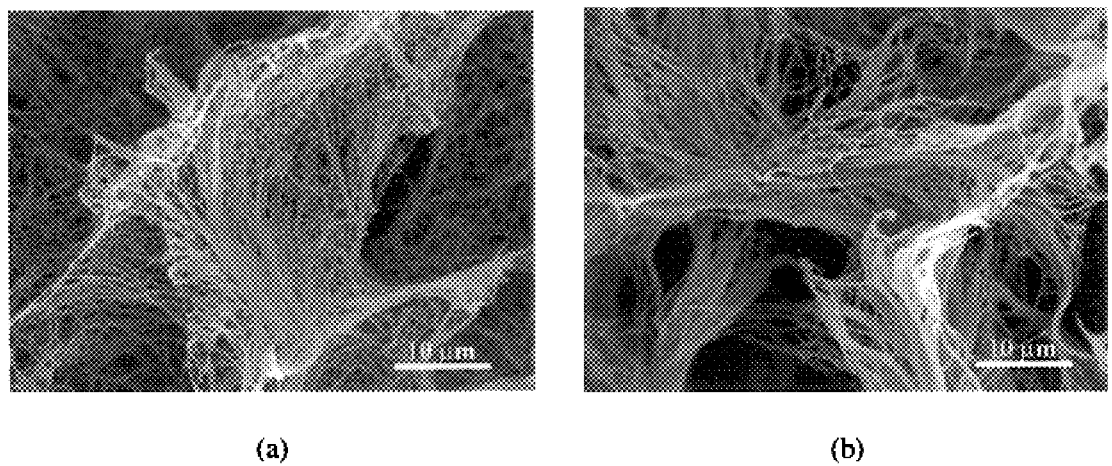

FIG. 10 presents a Scanning Electron Micrographs (SEMs), at a magnification of 2,000×, of a PLLA matrices prepared from a 2.5% (wt/v) PLLA/dioxane/methanol (dioxane/methanol=80/20) solution with a gelation temperature of −18° C.

(A) With water exchange.

(B) Without water exchange.

Figure 11:
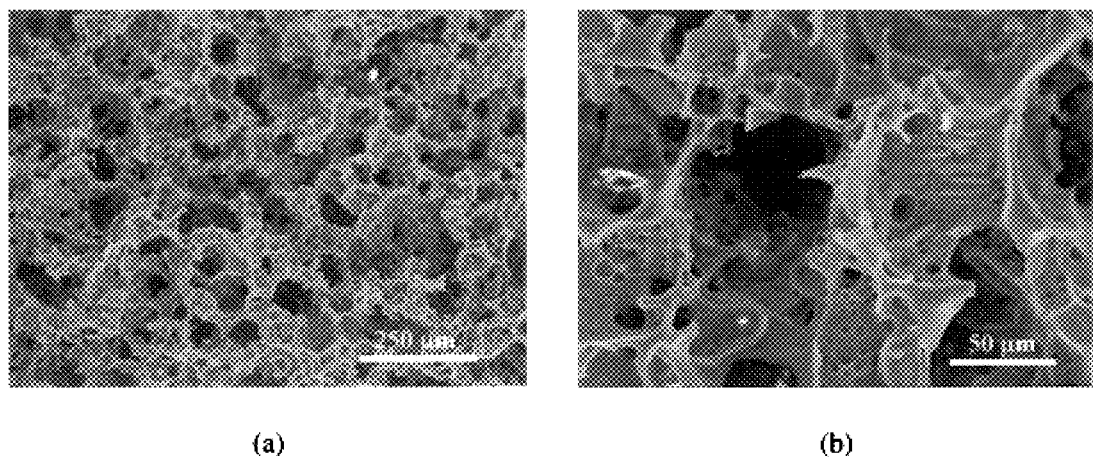

FIGS. 11A and 11B present Scanning Electron Micrographs (SEMs), at different magnifications, of porous matrices prepared from uncrystallizable aliphatic polyester solutions at a gelation temperature of −18° C.

Figure 12:
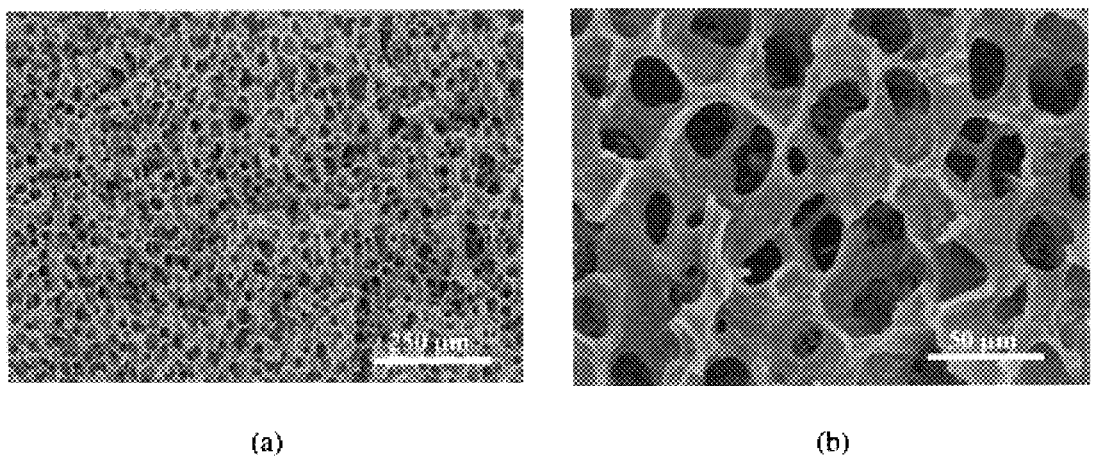

FIGS. 12A and 11B present Scanning Electron Micrographs (SEMs), at different magnifications, of a porous matrix prepared from uncrystallizable aliphatic polyester solutions at a gelation temperature of −18° C.

FIGS. 13A and 13B present a Scanning Electron Micrograph (SEM), at different magnifications, of a PLLA matrix prepared from a of 5% (wt/v) PLLA/THF/Salt mixture with a gelation temperature of −18° C.

DESCRIPTION OF THE INVENTION

The present invention relates to methods of fabrication for fibrillar matrices as well as the resulting fibrillar matrices as compositions suitable as a fibrillar matrix for cellular infiltration and ingrowth, the cultivation of cells within said matrices for the fabrication and repair of tissues and organs, and as biocompatible synthetic protheses. In addition, said fibrillar matrices have applications as biodegradable packaging materials. The present invention demonstrates that a variety of polymer sources and solvents may be used to construct a synthetic fibrillar matrix that approximates the morphology of a native collagenous extracellular matrix with a desired porosity.

While it is not intended that the present invention be limited to any specific mechanism, the gelation temperature of said polymer/solvent solution, the amount of time said polymer/solvent solutions are maintained at said gelation temperatures, and the concentration of polymer within said polymer/solvent solution are important considerations when a particular resulting fibrillar morphology is desired (comprising fiber diameter, porosity, and unit length) of the matrices recited in the instant invention.

Living cells may be incorporated into the solvent free fibrillar matrices and cultured in vitro. In the alternative, the fibrillar matrix may be maintained in an in vitro tissue culture environment. Depending on the selection of polymer source, a biodegradable fibrillar matrix may be created. Such biodegradable fibrillar matrices form a synthetic extracellular matrix (that approximates the morphology of a native collagenous extracellular matrix) resorbable by infiltrating cells. In the alternative, the present invention also contemplates biocompatible but non-biodegradable fibrillar matrices that approximates the morphology of a native tendons and facia.

These variations illustrate how a fibrillar matrix, that approximates the morphology of a native collagenous extracellular matrix with a desired fiber diameter, unit length, and porosity may be used as an tissue engineering scaffold. Given the availability of the material sources and relative ease in processing said materials into the instant fibrillar matrix that approximates the morphology of a native collagenous extracellular matrix, with a desired porosity, the instant invention is well suited to large-scale tissue engineering and manufacture.

EXPERIMENTAL

The following examples serve to illustrate certain preferred embodiments and aspects of the present invention and are not to be construed as limiting the scope thereof.

I. Materials

The following compounds are used as polymer sources. Poly(L-lactic acid) (PLLA) and poly(D,L-lactic acid-co-glycolic acid) (85/15) (PLGA) with an inherent viscosity of approximately 1.6 and 0.5–0.6 respectively are available from Boehringer Ingelheim (Ingelheim, Germany). Poly(D, L-lactic acid) (PDLLA) with a molecular weight of 103,000 is purchased from Sigma Chemical Co. (St. Louis, Mo.). PLLA, PLGA and PDLLA are used without further purification.

The following compounds are used as solvents: dioxane, a solution of dioxane and water, tetrahydrofuran (THF), N,N-dimethylformamide (DMF), pyridine, methanol and acetone. Deionized water is obtained with a Milli-Q water filter system from Millipore Corporation (Bedford, Mass.). The organic solvents may be obtained from Aldrich Chemical Company (Milwaukee, Wis.).

II. Methods

A. Porous Fibrillar Matrix Fabrication

1. Preparation of the Polymer/Solvent Solution

An aliquot from a given polymer source is weighed accurately into a flask. A given amount of solvent is then added into the flask to yield a solution with a desired concentration (from 1% (wt/v) to 15% (wt/v). Approximately two hours of magnetic stirring at 60° C. is required to obtain a homogeneous solution in a solution where the polymer concentration is less than or equal to 5%.

A given amount of said homogenous polymer/solvent solution, maintained at 50° C., is transferred into a mold of a desired shape. While it is not intended that the present invention be limited to a specific mold, in one example said mold is made of Teflon.

2. Gelation of the Polymer/Solvent Solution

The cast polymer/solvent solution is rapidly transferred into a refrigerator or a freezer to gel at a preferred temperature. The gelation time depends on temperature, solvent and polymer concentration of the polymer/solvent solution. See Table 2. The gel is kept at the gelling temperature for at least 2 hours after gelation.

3. Removal of Solvent from the Gelled Polymer

The cast containing the gel is immersed into distilled water to facilitate solvent exchange. The water is changed three times a day for two days. The hydrated solvent free gel is then removed from water, blotted to remove gross excess water, and transferred into a freezer at −18° C. for at least 2 hours.

4. Removal of Water from the Hydrated Gel

The frozen gel is transferred into a freeze-drying vessel maintained at −5 to −10° C., and is freeze-dried under vacuum lower than 0.5 mmHg for one week. The dried porous matrix is then stored in a desiccator until characterization.

B. Matrix Characterization

1. Thermodynamics

The melting behavior of the fibrillar matrices is characterized with a differential scanning calorimeter (DSC-7, Perkin-Elmer, Norwalk, Conn.). The calibration is performed using indium standards. A fibrillar matrix sample (5–10 mg) is used without any further thermal treatment. A heating rate of 20° C./min and a temperature range of 30–200° C. is used. The degree of crystallinity is calculated as: $X_c = \Delta H_m / \Delta H°_m$, where $\Delta H_m$ is the measured enthalpy of melting and $\Delta H°_m$ is the enthalpy of melting of 100% crystalline polymer. As an example, the $\Delta H°_m$ for PLLA is equal to 203.4 J/g.

2. Density and Porosity

The estimated densities and porosities of the fibrillar matrices is obtained as follows. Circular discs of the fibrillar matrix are fabricated as previously described. The radius and height of a disc is measured to calculate the volume according to the equation $\pi r^2 \cdot h$. The weight of the specimen is measured with an analytical balance. The density is calculated from the volume and weight. The porosity, $\epsilon$, is calculated from the measured overall densities $D_f$ of the fibrous matrix and the skeletal density $D_p$:

$$\varepsilon = \frac{D_p - D_f}{D_p} \tag{1}$$

For the fibrillar matrix, the skeletal density is the density of the polymer, which is given by:

$$D_p = \frac{1}{\frac{1-X_c}{D_a} + \frac{X_c}{D_c}} \tag{2}$$

where $X_c$ is the degree of polymer crystallinity. As an example, $D_a$ for PLLA=1.248 g/ml (density of amorphous polymer) and $D_c$ for PLLA=1.290 g/ml (density of 100% crystalline polymer).

3. Morphology

The morphologies of the fibrillar matrices are studied with a scanning electron microscopy (SEM) (S-3200N, Hitachi, Japan) at 15 kV. A specimen is cut with a razor blade or fractured after being frozen in liquid nitrogen for 5 minutes, and is then coated with gold using a sputter coater (Desk-II, Denton Vacuum Inc.). During said coating protocol, the gas pressure is lower than 50 mtorr, and the current is about 40 mA. The coating time is 200 seconds.

The average fiber diameter is calculated from the SEM micrographs. The surface area to volume ratio is estimated based on the average fiber diameter. In determining the surface area to volume ratio, the surface areas of the fiber ends are neglected based on a very large aspect ratio of the fibers (virtually a continuous fiber network) so that the surface area of a fiber was calculated with the equation:

$$A_f = \pi \cdot d \cdot l \tag{3}$$

where d is the diameter of the fiber and l is the length of the fiber. The volume of a fiber is given by:

$$V_f = \frac{\pi \cdot d^2 \cdot l}{4} \tag{4}$$

Therefore the surface to volume ratio is given by:

$$\frac{A_f}{V_f} = \frac{\pi \cdot d \cdot l}{\frac{\pi \cdot d^2 \cdot l}{4}} = \frac{4}{d} \quad (5)$$

Figure 1B:
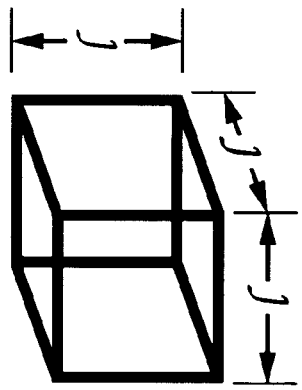
FIG. 1 shows a cubic fiber network model of (A) and array of cubic units and (B) an expanded view of a single isolated cubic unit.
Figure 1A:
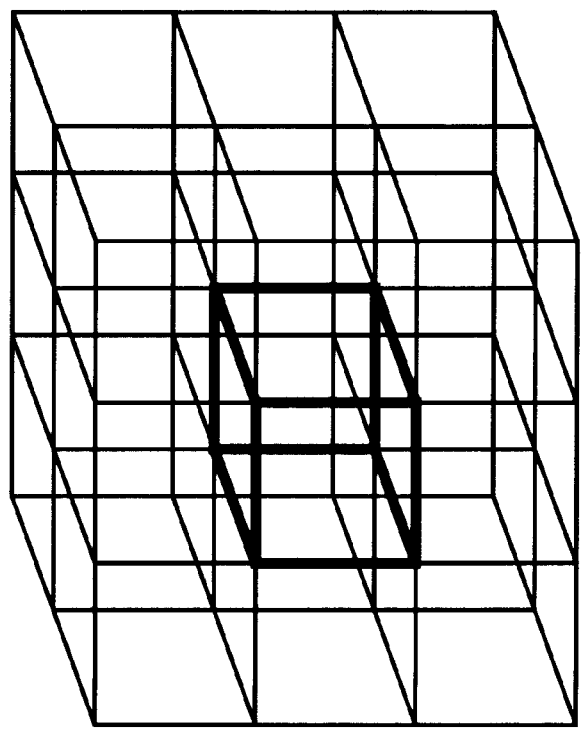

To quantify the fiber network density, the fiber length between two conjunctions (unit length) is estimated based on a simplified cubic structure model. See FIG. 1. This calculation pre-supposes a cubic network. There are 12 unit fibers bordering each unit cube. Each of these fibers is shared by 4 unit cubes. Therefore, there are 3 unit fibers in each unit cube. The porosity of the fiber network is given by:

$$\epsilon = 1 - \frac{3V_f}{V_c} \quad (6)$$

where $V_f$ is the volume of one unit fiber, and $V_c$ is the volume of the unit cube. Substituting equation (4) and $V_c = l^3$ into equation (6), the porosity is given by:

$$\epsilon = 1 - \frac{\frac{3\pi \cdot d^2 \cdot l}{4}}{l^3} \quad (7)$$

The unit length is given by rearranging equation (7), $$l = \frac{d}{2}\sqrt{\frac{3\pi}{1-\epsilon}} \quad (8)$$

When the fiber diameters are compared, a two-tail student's t-test (assuming equal variances) is performed to determine the statistical significance (p<0.05).

4. Mechanical Properties

Uniaxial tensile mechanical testing, with an Instron 4502 mechanical tester (Instron Corporation, Canton, Mass.), is performed to measure the mechanical properties of the fibrillar matrices. Matrix sheets with dimensions of 90×60×3 mm³ were prepared, and then cut into 90×10×3 mm³ strips for mechanical testing. A gauge length of 40 mm and a crosshead speed of 5 mm/min were used.

5. Effect of Gelation Conditions on Matrix Structure

The conditions under which said polymer/solvent gel is critical to achieving the fibrillar morphology of the matrix recited in the present invention. While it is not intended the present invention be limited to one specific gelation protocol or set of reagents, the relationship between conditions of gelation and the morphologies of the resultant polymer matrices are illustrated through the following examples.

a. The Effect of Gelation Temperature and Annealing Conditions on Matrix Structure Gelling temperature is an important factor controlling the porous fibrillar morphology of the matrices. For example, the matrix structure formed via gelation of 5% PLLA/THF solution at 23° C. or 19° C. is different from the matrix structure formed at lower gelation temperatures. At a gelation temperature of 23° C., no fibrillar structure was observed. Indeed at 23° C. the resulting matrix, composed of irregular platelets and pores, is unsuitable as a scaffold for cellular infiltration and ingrowth, the cultivation of cells within said matrices for the fabrication and repair of tissues and organs, and as biocompatible synthetic prosthesis.

Figure 2:
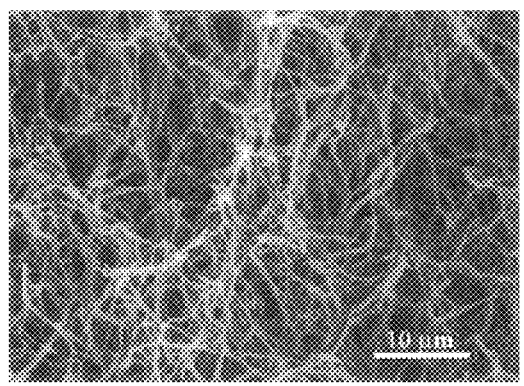
FIG. 2 shows Scanning Electron Micrographs (SEMs), at a magnification of 2,000×, of PLLA fibrillar matrices prepared at different gelation temperatures from a 5% (wt/v) solution of PLLA/THF; (A) 15° C., (B) 8° C., (C) −18° C., and (D) −195.8° C.
Figure 2:
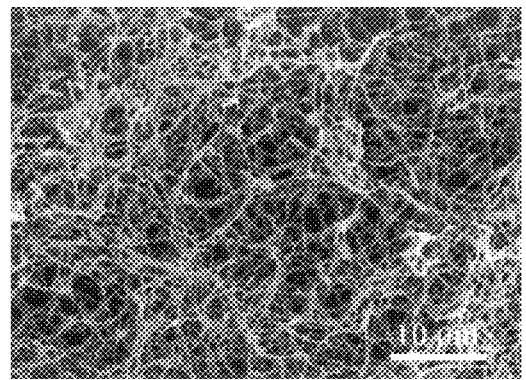
Figure 2:
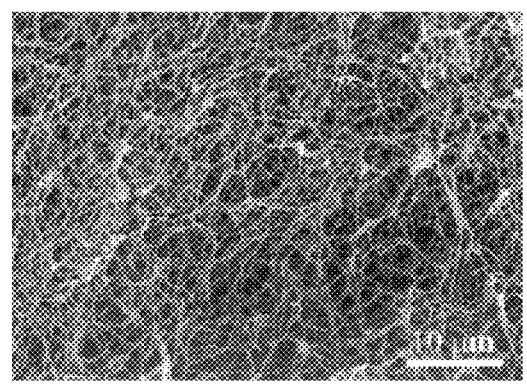
Figure 2:
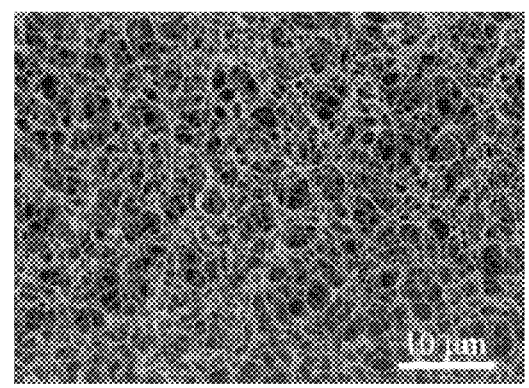
Figure 3:
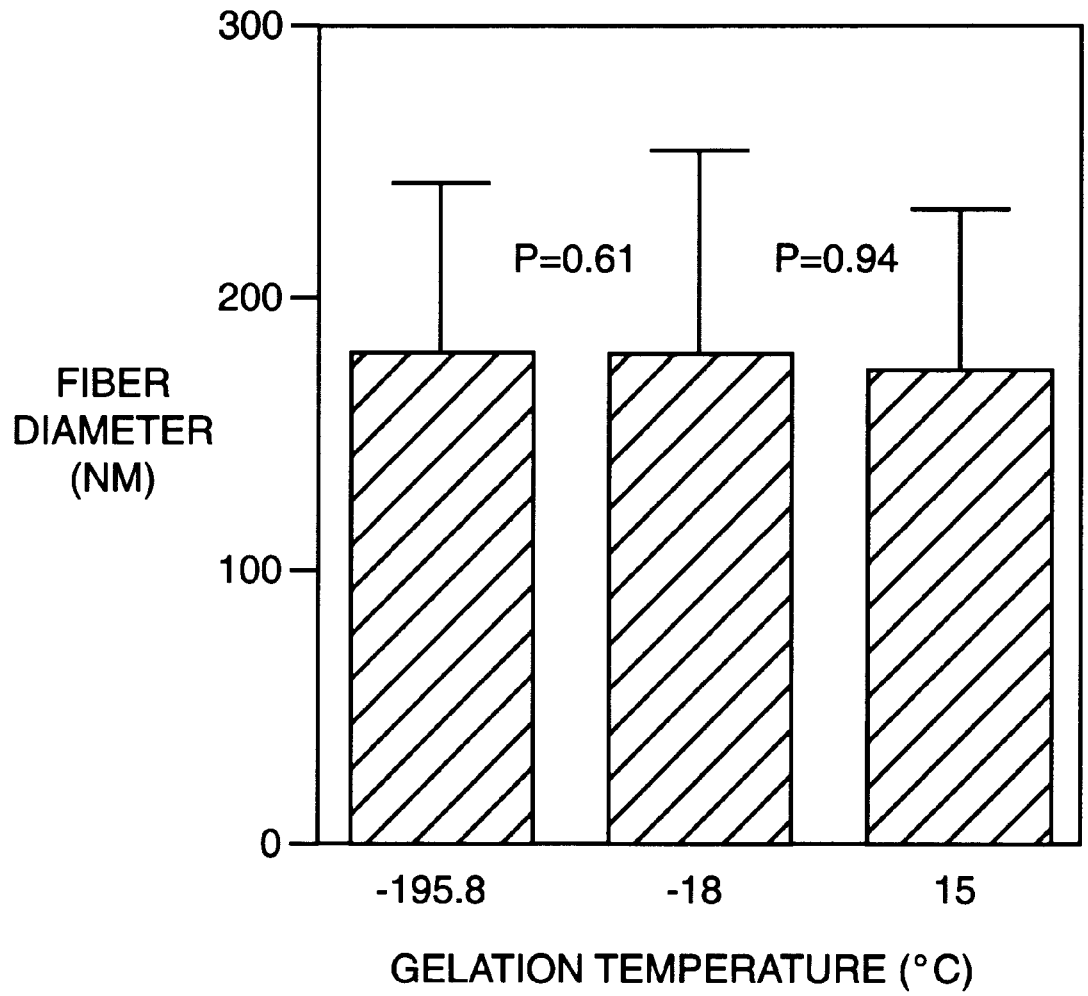
FIG. 3 presents a graph showing the relationship between the fiber diameter of a PLLA matrix, prepared from a 5.0% (wt/v) PLLA/THF solution, and gelation temperature with p values obtained from a two-tail student's t-test comparing fiber diameters of PLLA matrices.

In contrast, for matrices formed after PLLA/THF gelation at lower temperatures, e.g., 15° C., 8° C., –18° C., and –195.8° C. (liquid nitrogen), a three-dimensional nano fiber network is formed. See FIG. 2. The diameter of fibers within a matrix formed after PLLA gelation at these temperatures (e.g., 15° C., 8° C., –18° C., –195.8° C.) does not statistically vary. See FIG. 3. However, interfiber spacing becomes more uniform as the gelation temperature decreases (e.g., 15° C., 8° C., –18° C., –195.8° C.). See FIGS. 2a, 2b, 2c, and 2d.

b. The Effect of Polymer Concentration on Matrix Structure

Figure 4:
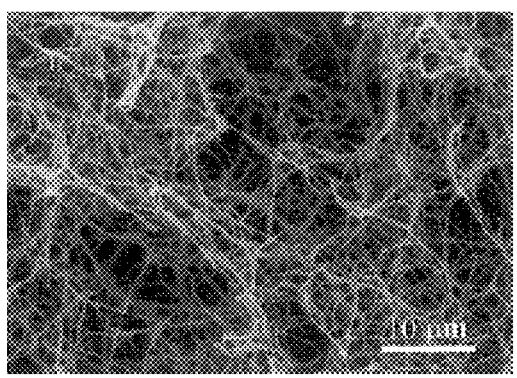
FIG. 4 shows SEM's, at a magnification of 2,000×, of PLLA fibrillar matrices prepared from PLLA/THF solutions (wt/v) with different PLLA concentrations at a gelation temperature of 8° C.; (A) 1.0%, (B) 2.5%, (C) 5.0% and (D) 7.5%.
Figure 4:
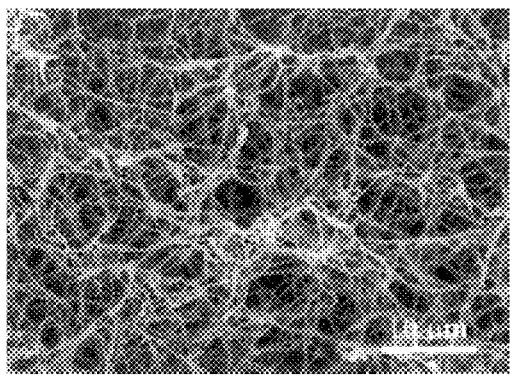
Figure 4:
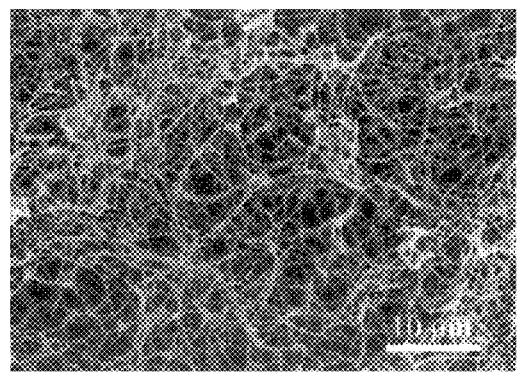
Figure 4:
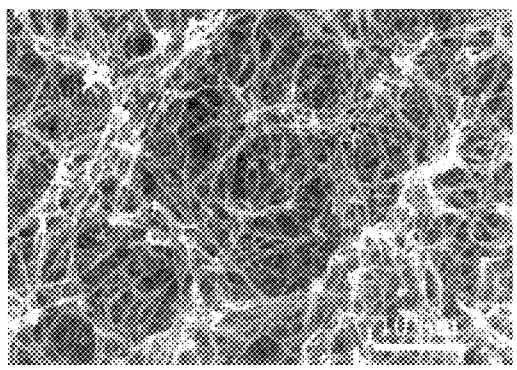
Figure 5:
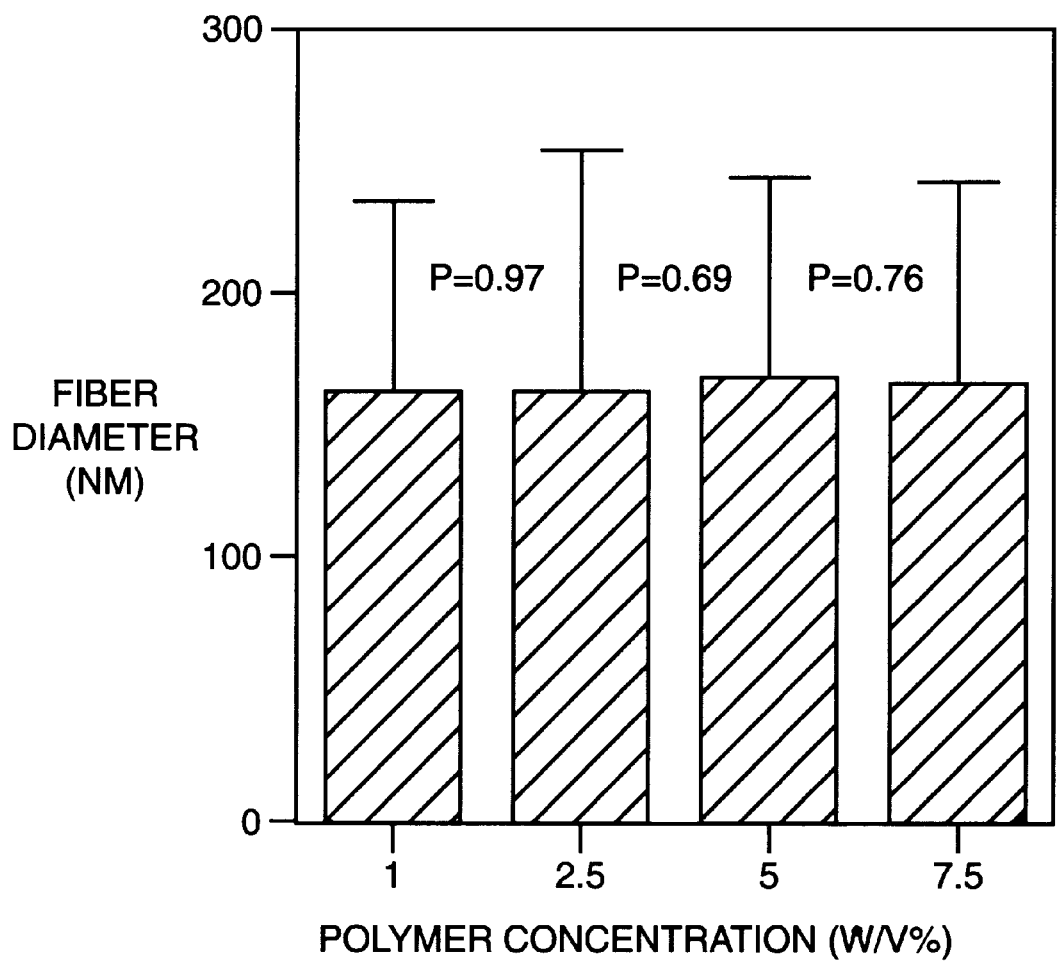
FIG. 5 presents a graph showing the relationship between the fiber diameter of a PLLA matrices prepared from PLLA/THF solutions with different PLLA concentrations [1%, 2.5%, 5%, and 7.5% (wt/v)] at a gelation temperature of 8° C. with p values obtained from a two-tail student's t-test comparing fiber diameters of PLLA matrices.

The average fiber diameter of fibrillar matrices do not statistically vary with the concentration of polymer solution used to fabricate the matrices in selected concentration ranges. See FIGS. 4 and 5. In contrast, the average unit length decreases with increasing polymer concentration. See Table 3.

Furthermore at low polymer concentrations, such as 1% PLLA/THF solution, relatively large pores are observed with nonuniform interfiber spacing. See FIG. 4a. In contrast, with increased polymer concentration, pore structure becomes increasingly uniform and the average unit length decreases. See Table 3.

Figure 6:
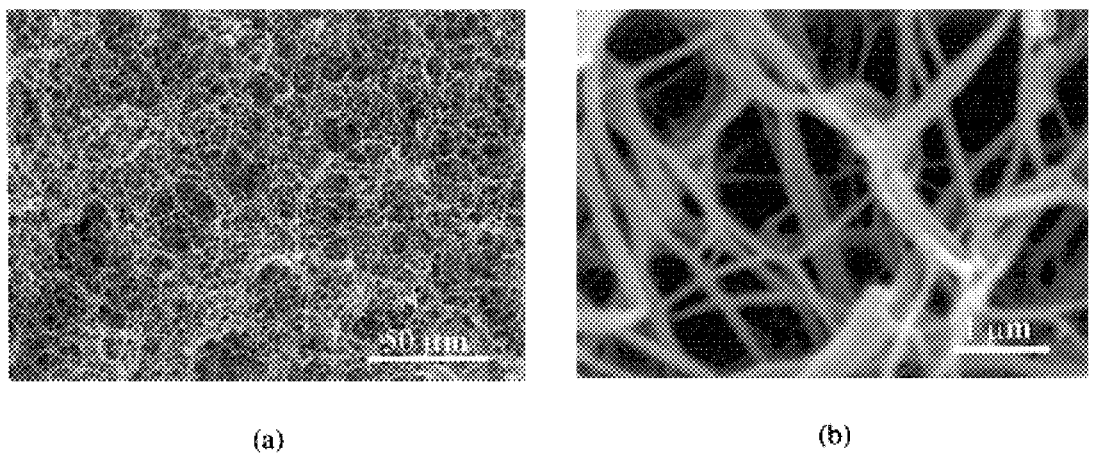
FIG. 6 shows SEM's of a PLLA fibrillar matrix prepared from a 2.5 (wt/v) PLLA/THF solution at a gelation temperature of 8° C. at different magnifications; (A) 500× and (B) 20,000×.

These morphological observations are consistent with the porosity and density data presented in Table 1 and Table 3. These data present density and porosity parameters in a series of fibrillar matrices, with fiber diameters ranging between 50 to 500 nm, created from biodegradable aliphatic polyesters comprising a three-dimensional continuous fibrous network that approximates the morphology of a native collagenous extracellular matrix. See FIG. 6.

In addition, the surface/volume ratio of the instant fibrillar matrices do not change significantly with the polymer concentration because the fiber diameter (160–170 nm) does not change with polymer concentration. See Table 3.

Figure 7A:
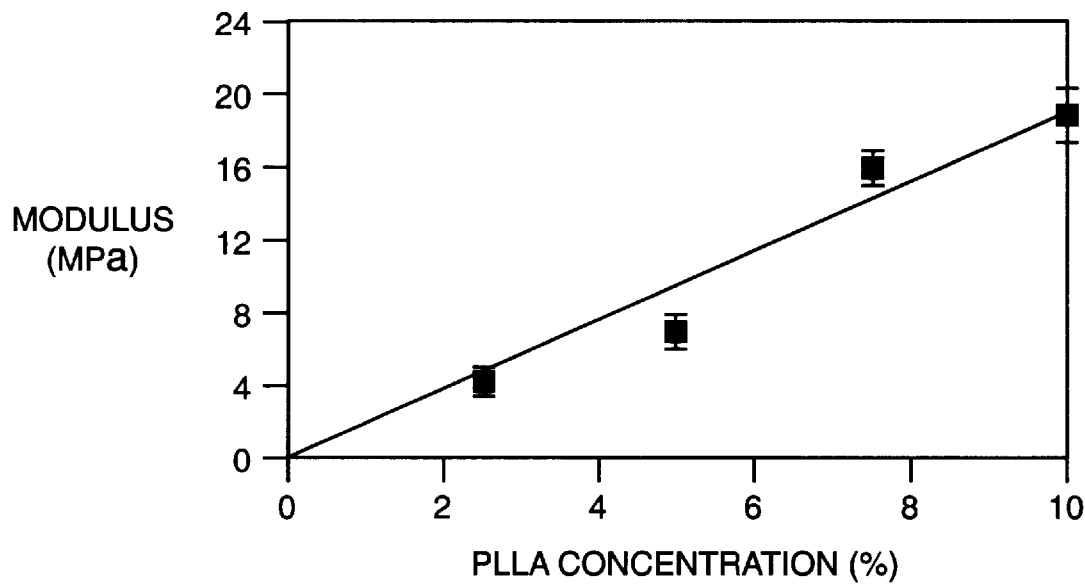
FIG. 7 presents data on the mechanical properties of fibrous PLLA matrices prepared from PLLA/THF solutions with varying PLLA concentrations at a gelation temperature of −18° C.; (A) Modulus, (B) Tensile Strength, and (C) Elongation at break.
Figure 7B:
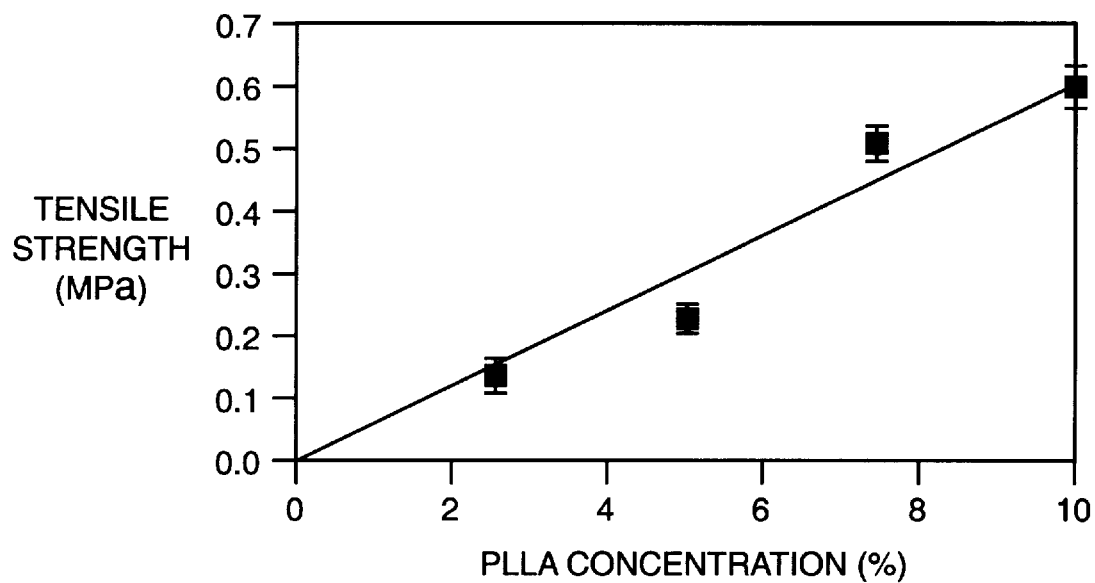
Figure 7C:
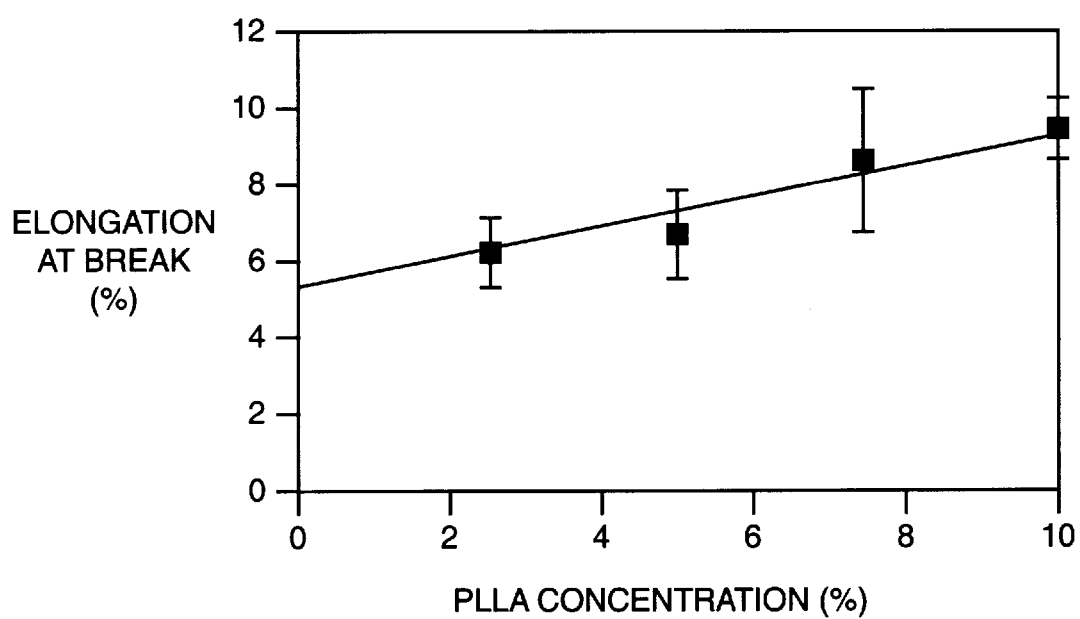

Young's modulus, tensile strength, and elongation at break all increase with polymer concentration. See FIG. 7. In contrast, the platelet-like matrices (created at higher gelation temperatures) are too fragile to measure these same mechanical properties.

The melting point, enthalpy of melting, and the degree of crystallinity of the matrices prepared from PLLA/THF solution with different PLLA concentrations and at different gelling temperatures is presented in Table 4. At a gelation temperature of –18° C., the melting point and the degree of crystallinity of PLLA matrices do not change significantly with the polymer concentration. Similarly, the degree of crystallinity does not change significantly in a gelation temperature range of 15° C. or below. In contrast, however, the matrix formed at a higher temperature (e.g., room temperature) has a higher degree of crystallinity than matrices formed at low gelation temperatures. See Table 4.

c. The Effect of Thermal History on Matrix Morphology

Thermal history also effects matrix morphology. For example, both platelet-like and nano fiber-like structures are observed in a matrix prepared by gelling a 5% PLLA/THF solution at room temperature for 2 or 12 hours and then quenching at –18° C. See FIGS. 8a and b. The percentage of platelet-like structures increases as a function of time the PLLA/THF solution gels at room temperature. For example, after gelling at room temperature (and subsequent maintenance at room temperature for a total of 24 hours); a platelet-like morphology is observed exclusively with or without subsequent quenching to –18° C. See FIG. 8c. In contrast, when the 5% PLLA/THF solution is quenched to –18° C. for 10 minutes at first and then returned to room temperature for one week, the resulting morphology is a fibrillar matrix. See FIG. 8d.

7. Incorporation of Cells into a Fibrillar Matrix

Fibroblasts are cultured and expanded in tissue culture medium. The cultured cells are trypsinized with trypsin-EDTA and are washed twice with DPBS. The cells are then suspended in "complete medium" (89% DMEM, 10% FBS, 1% P/S, and 50 mg/L L-ascorbic acid) at a density of $1 \times 10^7$ cells/ml. Circular discs with a diameter of 10 mm and a thickness of 1.5 mm are cut from a fibrillar matrix sheet and one disc is fit in each well of a customer-made twelve-well Teflon culture plate. $1.5 \times 10^6$ cells in total of 0.5 ml complete medium are added to each of the matrix discs. They are cultured in a humidified incubator at 37° C. in the presence of 5% $CO_2$. The medium (0.5 ml each) is changed daily. Two weeks later, cell infiltrated matrix is fixed in 10% neutral buffered formalin, embedded in paraffin, and cut into 5 $\mu$m cross sections for histological analysis. The fibroblast are normal in appearance, having penetrated into the fibrillar matrix.

EXAMPLE 1

PLLA Fibrillar Matrix from 1.0% PLLA/THF Solution with a Gelation Temperature of 8° C.

0.2 gram poly(L-lactic acid) (PLLA) was added into a flask containing 20 ml THF, and then stirred with a magnetic stirrer at about 60° C. to make a solution with a concentration of 1.0 (wt/v)%. 2 ml of the prepared solution (prewarmed to 50° C.) was added into a Teflon vial. The vial containing PLLA solution was then rapidly transferred into a refrigerator and kept at 8° C. for 3 hours to gel. After gelation, the gel was kept at 8° C. for another 4 hours before the next step. The vial containing the gel was immersed into distilled water for solvent exchange. The water was changed three times a day for two days. The gel was removed from the water and blotted with a piece of filter paper, and then transferred into a freezer at −20° C. for at least 2 hours to completely freeze the water-containing gel. The frozen gel was transferred into a freeze-drying vessel at −5∼−10° C., in an ice/salt bath, and was freeze-dried at a vacuum lower than 0.5 mmHg for one week. The resulting fibrillar matrix was observed with SEM (FIG. 4a).

EXAMPLE 2

PLLA Fibrillar Matrix from 2.5% PLLA/THF Solution with a Gelation Temperature of 8° C.

0.5 gram poly(L-lactic acid) (PLLA) was added into a flask containing 20 ml THF, and then stirred with a magnetic stirrer at about 60° C. to make a solution with a concentration of 2.5 (wt/v)%. 2 ml of the prepared solution (prewarmed to 50° C.) was added into a Teflon vial. The vial containing PLLA solution was then rapidly transferred into a refrigerator and kept at 8° C. for 1 hour to gel. After gelation, the gel was kept at 8° C. for another 2 hours before the next step. The vial containing the gel was immersed into distilled water for solvent exchange. The water was changed three times a day for two days. The gel was removed from the water and blotted with a piece of filter paper, and then transferred into a freezer at −20° C. for at least 2 hours to completely freeze the water-containing gel. The frozen gel was transferred into a freeze-drying vessel at −5∼−10° C., in an ice/salt bath, and was freeze-dried at a vacuum lower than 0.5 mmHg for one week. The resulting fibrillar matrix was observed with SEM (FIG. 4b).

EXAMPLE 3

PLLA Fibrillar Matrix from 5.0% PLLA/THF Solution with a Gelation Temperature of 8° C.

1.0 gram poly(L-lactic acid) (PLLA) was added into a flask containing 20 ml THF, and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was then rapidly transferred into a refrigerator and kept at 8° C. for 1 hour to gel. After gelation, the gel was kept at 8° C. for another 2 hours before the next step. The vial containing the gel was immersed into distilled water for solvent exchange. The water was changed three times a day for two days. The gel was removed from the water and blotted with a piece of filter paper, and then transferred into a freezer at −20° C. for at least 2 hours to completely freeze the water-containing gel. The frozen gel was transferred into a freeze-drying vessel at −5∼−10° C., in an ice/salt bath, and was freeze-dried at a vacuum lower than 0.5 mmHg for one week. The resulting fibrillar matrix was observed with SEM (FIG. 4c).

EXAMPLE 4

PLLA Fibrillar Matrix from 7.5% PLLA/THF Solution with a Gelation Temperature of 8° C.

1.5 grams poly(L-lactic acid) (PLLA) was added into a flask containing 20 ml THF, and then stirred with a magnetic stirrer at about 60° C. to make a solution with a concentration of 7.5 (wt/v)%. 2 ml of the prepared solution (prewarmed to 50° C.) was added into a Teflon vial. The vial containing PLLA solution was then rapidly transferred into a refrigerator and kept at 8° C. for 1 hour to gel. After gelation, the gel was kept at 8° C. for another 2 hours before the next step. The vial containing the gel was immersed into distilled water for solvent exchange. The water was changed three times a day for two days. The gel was removed from the water and blotted with a piece of filter paper, and then transferred into a freezer at −20° C. for at least 2 hours to completely freeze the water-containing gel. The frozen gel was transferred into a freeze-drying vessel at −5∼−10° C., in an ice/salt bath, and was freeze-dried at a vacuum lower than 0.5 mmHg for one week. The resulting fibrillar matrix was observed with SEM (FIG. 4d).

EXAMPLE 5

PLLA Fibrillar Matrix from 5.0% PLLA/THF Solution with a Gelation Temperature of 15° C.

1.0 gram poly(L-lactic acid) (PLLA) was added into a flask containing 20 ml THF, and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was then rapidly transferred into a water bath at 15° C. for 1 hour to gel. After gelation, the gel was kept at 15° C. for another 2 hours before the next step. The vial containing the gel was immersed into distilled water for solvent exchange. The water was changed three times a day for two days. The gel was removed from the water and blotted with a piece of filter paper, and then transferred into a freezer at −20° C. for at least 2 hours to completely freeze the water-containing gel. The frozen gel was transferred into a freeze-drying vessel at −5∼−10° C., in an ice/salt bath, and was freeze-dried at a vacuum lower than 0.5 mmHg for one week. The resulting fibrillar matrix was observed with SEM (FIG. 2a).

EXAMPLE 6

PLLA Fibrillar Matrix from 5.0% PLLA/THF Solution with a Gelation Temperature of −18° C.

1.0 gram poly(L-lactic acid) (PLLA) was added into a flask containing 20 ml THF, and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was then rapidly transferred into a freezer at −18° C. for 30 minutes to gel. After gelation, the gel was kept at −18° C. for another 2 hours before the next step. The vial containing the gel was immersed into distilled water for solvent exchange. The water was changed three times a day for two days. The gel was removed from the water and blotted with a piece of filter paper, and then transferred into a freezer at −20° C. for at least 2 hours to deep freeze the water-containing gel. The frozen gel was transferred into a freeze-drying vessel at −5~−10° C., in an ice/salt bath, and was freeze-dried at a vacuum lower than 0.5 mmHg for one week. The resulting fibrillar matrix structure was observed with SEM (FIG. 2c).

EXAMPLE 7

PLLA Fibrillar Matrix from 5.0% PLLA/THF Solution Frozen with Liquid Nitrogen 1.0 gram poly(L-lactic acid) (PLLA) was added into a flask containing 20 ml THF, and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was then rapidly immersed into liquid nitrogen for one hour. The vial containing the gel was immersed into distilled water for solvent exchange. The water was changed three times a day for two days. The gel was removed from the water and blotted with a piece of filter paper, and then transferred into a freezer at −20° C. for at least 2 hours to deep freeze the water-containing gel. The frozen gel was transferred into a freeze-drying vessel at −5~−10° C., in an ice/salt bath, and was freeze-dried at a vacuum lower than 0.5 mmHg for one week. The resulting fibrillar matrix was observed with SEM (FIG. 2d).

EXAMPLE 8

Figure 8:
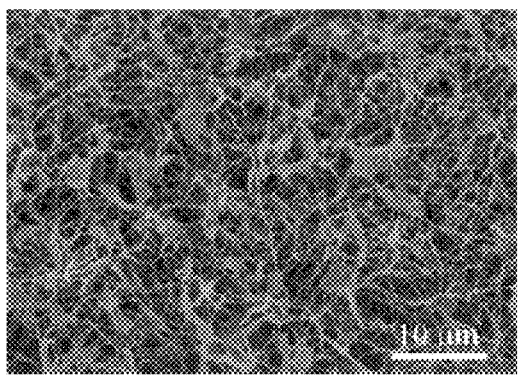
FIG. 8 shows SEM micrographs, at a magnification of 2,000×, of PLLA matrices prepared from a 5.0% (wt/v) PLLA/THF solution with different thermal gelation histories.
Figure 8:
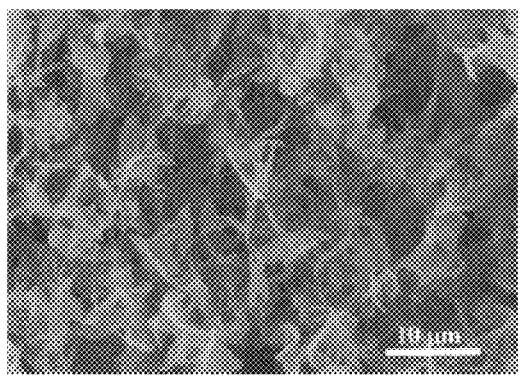
Figure 8:
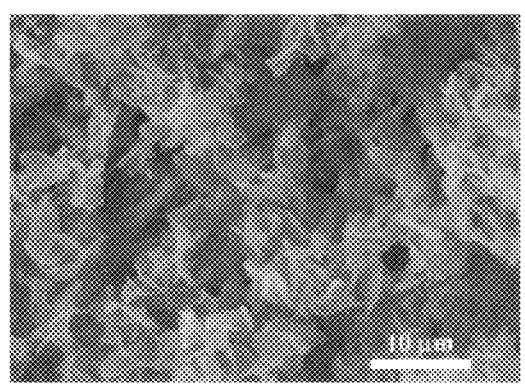
Figure 8:
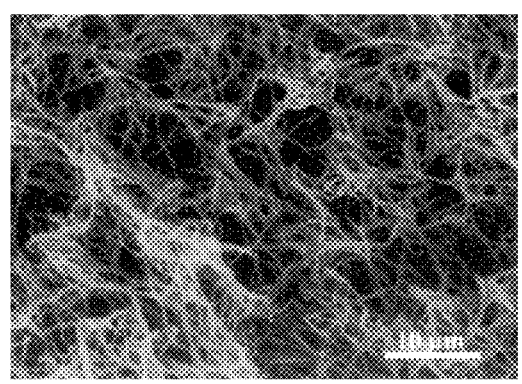

PLLA Fibrillar Matrix from 5.0% PLLA/THF Solution with Two Gelation Temperatures 1.0 gram poly(L-lactic acid) (PLLA) was added into a flask containing 20 ml THF, and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was kept at room temperature (23° C.) for two hours and then rapidly transferred into a freezer at −18° C. for 30 minutes to gel. After gelation, the gel was kept at −18° C. for another 2 hours before the next step. The vial containing the gel was immersed into distilled water for solvent exchange. The water was changed three times a day for two days. The gel was removed from the water and blotted with a piece of filter paper, and then transferred into a freezer at −20° C. for at least 2 hours to deep freeze the water-containing gel. The frozen gel was transferred into a freeze-drying vessel at −5~−10° C., in an ice/salt bath, and was freeze-dried at a vacuum lower than 0.5 mmHg for one week. The resulting fibrillar matrix was observed with SEM (FIG. 8a).

EXAMPLE 9

PLLA Fibrillar Matrix from 5.0% PLLA/THF Solution with Two Gelation Temperatures 1.0 gram poly(L-lactic acid) (PLLA) was added into a flask containing 20 ml THF, and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was kept at room temperature (23° C.) for 24 hours and then rapidly transferred into a freezer at −18° C. for 2 hours before the next step. The vial containing the gel was immersed into distilled water for solvent exchange. The water was changed three times a day for two days. The gel was removed from the water and blotted with a piece of filter paper, and then transferred into a freezer at −20° C. for at least 2 hours to completely freeze the water-containing gel. The frozen gel was transferred into a freeze-drying vessel at −5~−10° C., in an ice/salt bath, and was freeze-dried at a vacuum lower than 0.5 mmHg for one week. The resulting structure was observed with SEM (FIG. 8c).

EXAMPLE 10

PLLA Fibrillar Matrix from 5.0% PLLA/THF Solution with Two Gelation Temperatures 1.0 gram poly(L-lactic acid) (PLLA) was added into a flask containing 20 ml THF, and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was rapidly transferred into a freezer at −18° C. for 10 minutes to gel and then kept at room temperature (23° C.) for one week. The vial containing the gel was immersed into distilled water for solvent exchange. The water was changed three times a day for two days. The gel was removed from the water and blotted with a piece of filter paper, and then transferred into a freezer at −20° C. for at least 2 hours to deep freeze the water-containing gel. The frozen gel was transferred into a freeze-drying vessel at −5~−10° C., in an ice/salt bath, and was freeze-dried at a vacuum lower than 0.5 mmHg for one week. The resulting fibrillar matrix was observed with SEM (FIG. 8d).

EXAMPLE 11

PLLA Fibrillar Matrix from 5.0% PLLA/THF/ methanol Solution Frozen with Liquid Nitrogen 1.0 gram poly(L-lactic acid) (PLLA) was added into a flask containing 20 ml mixture of THF and methanol (THF/methanol=80/20), and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was then rapidly immersed into liquid nitrogen for one hour. The vial containing the gel was immersed into distilled water for solvent exchange. The water was changed three times a day for two days. The gel was removed from the water and blotted with a piece of filter paper, and then transferred into a freezer at −20° C. for at least 2 hours to deep freeze the water-containing gel. The frozen gel was transferred into a freeze-drying vessel at −5~−10° C., in an ice/salt bath, and was freeze-dried at a vacuum lower than 0.5 mmHg for one week. The nano-fibrous matrix structure was observed with SEM (FIG. 9).

EXAMPLE 12

PLLA Fibrillar Matrix from 2.5% PLLA/Dioxane/ Methanol Solution with a Gelation Temperature of −18° C. with Water Exchange 1.0 gram poly(L-lactic acid) (PLLA) was added into a flask containing 20 ml mixture of dioxane and methanol (dioxane/methanol=80/20), and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was then rapidly transferred into a freezer at −18° C. for 1 hour to gel. After gelation, the gel was kept at −18° C. for another 2 hours before the next step. The vial containing the gel was immersed into distilled water for solvent exchange. The water was changed three times a day for two days. The gel was removed from the water and blotted with a piece of filter paper, and then transferred into a freezer at −20° C. for at least 2 hours to deep freeze the water-containing gel. The frozen gel was transferred into a freeze-drying vessel at −5~−10° C., in an ice/salt bath, and was freeze-dried at a vacuum lower than 0.5 mmHg for one week. The resulting matrix was observed with SEM (FIG. 10a).

EXAMPLE 13

PLLA Fibrillar Matrix from 2.5% PLLA/Dioxane/Methanol Solution with a Gelation Temperature of −18° C. without Water Exchange 1.0 gram poly(L-lactic acid) (PLLA) was added into a flask containing 20 ml mixture of dioxane and methanol (dioxane/methanol=80/20), and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was then rapidly transferred into a freezer at −18° C. for 1 hour to gel. After gelation, the gel was kept at −18° C. for another 2 hours before the next step. The gel was directly transferred into a freeze-drying vessel at −5~−10° C., in an ice/salt bath, and was freeze-dried at a vacuum lower than 0.5 mmHg for one week. The resulting fibrillar matrix was observed with SEM (FIG. 10b).

EXAMPLE 14

PDLLA Foam from PDLLA/dioxane/H$_2$O Solution with a Gelation Temperature of −18° C.

1.0 gram poly(D,L-lactic acid) (PDLLA) was added into a flask containing 20 ml mixture of dioxane and H$_2$O (dioxane/H$_2$O=85/15), and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was then rapidly transferred into a refrigerator and kept at −18° C. for 1 hour to gel. After gelation, the gel was kept at −18° C. for another 2 hours before the next step. The vial containing the gel was immersed into distilled water for solvent exchange. The water was changed three times a day for two days. The gel was removed from the water and blotted with a piece of filter paper, and then transferred into a freezer at −20° C. for at least 2 hours to deep freeze the water-containing gel. The frozen gel was transferred into a freeze-drying vessel at −5~−10° C., in an ice/salt bath, and was freeze-dried at a vacuum lower than 0.5 mmHg for one week. The resulting structure was observed with SEM (FIG. 11a and 11b).

EXAMPLE 15

PLGA Foam from PLGA/Dioxane/H$_2$O Solution with a Gelation Temperature of −18° C.

1.0 gram poly(D,L-lactide-co-glycolide) (PLGA) was added into a flask containing 20 ml mixture of dioxane and H$_2$O (dioxane/H$_2$O=80/20), and then stirred with a magnetic stirrer at about 60° C. to make a solution with a concentration of 5.0 (wt/v)%. 2 ml of the prepared solution (prewarmed to 50° C.) was added into a Teflon vial. The vial containing PLLA solution was then rapidly transferred into a refrigerator and kept at −18° C. for 1 hour to gel. After gelation, the gel was kept at −18° C. for another 2 hours before the next step. The vial containing the gel was immersed into distilled water for solvent exchange. The water was changed three times a day for two days. The gel was removed from the water and blotted with a piece of filter paper, and then transferred into a freezer at −20° C. for at least 2 hours to completely freeze the water-containing gel. The frozen gel was transferred into a freeze-drying vessel at −5~−10° C., in an ice/salt bath, and was freeze-dried at a vacuum lower than 0.5 mmHg for one week. The resulting foam was observed with SEM (FIG. 12a and 12b).

EXAMPLE 16

PLLA Fibrillar Matrix from 5.0% PLLA/THF/Salt Mixture with a Gelation Temperature of −18° C.

Figure 13:
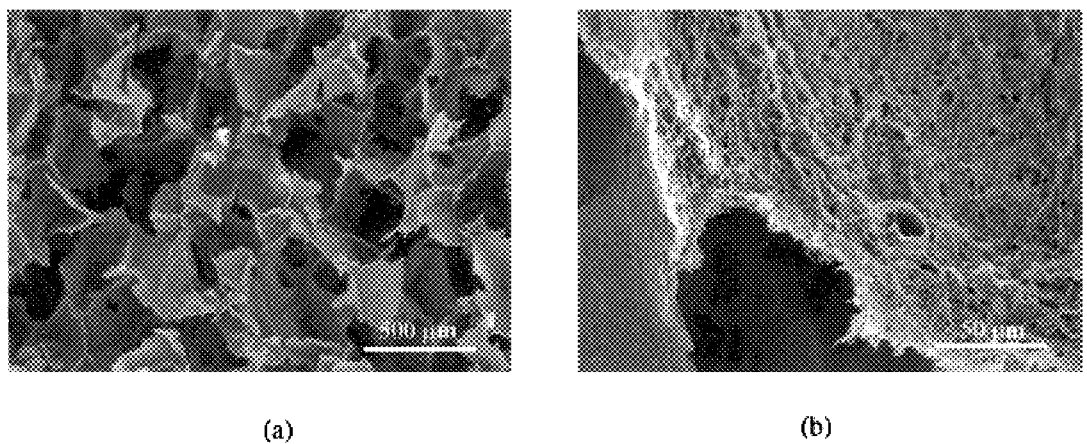

1.0 gram poly(L-lactic acid) (PLLA) was added into a flask containing 20 ml THF, and then stirred with a magnetic stirrer at about 60° C. to make a solution with a concentration of 5.0 (wt/v)%. 0.6 ml of the prepared solution (prewarmed to 50° C.) was pipetted and dripped slowly into a Teflon vial containing 2.0 grams of salt particles with desired size. The vial containing PLLA solution and particles was then rapidly transferred into a freezer at −18° C. and kept for 30 minutes to gel. After gelation, the gel was kept at −18° C. for another 2 hours before the next step. The vial containing the gel and salt particles was immersed into distilled water for solvent exchange and salt particles leaching. The water was changed three times a day for two days. The gel was removed from the water and blotted with a piece of filter paper, and then transferred into a freezer at −20° C. for at least 2 hours to completely freeze the water-containing gel. The frozen gel was transferred into a freeze-drying vessel at −5~−10° C., in an ice/salt bath, and was freeze-dried at a vacuum lower than 0.5 mmHg for one week. The resulting matrix was observed with SEM (FIG. 13).

TABLE 1

| Polymer Concentration | Gelling Temperature | | | | | |
| --- | --- | --- | --- | --- | --- | --- |
| | −18° C. | | 8° C. | | 23° C. | |
| | Density (g/ml) | Porosity (%) | Density (g/ml) | Porosity (%) | Density (g/ml) | Porosity (%) |
| PLLA/THF 1.0% | 0.0183 | 98.5 | 0.0186 | 98.5 | N/A | N/A |
| PLLA/THF 2.5% | 0.0393 | 96.9 | 0.0328 | 97.4 | N/A | N/A |

TABLE 1-continued

| | Gelling Temperature | | | | | |
|---|---|---|---|---|---|---|
| | −18° C. | | 8° C. | | 23° C. | |
| Polymer Concentration | Density (g/ml) | Porosity (%) | Density (g/ml) | Porosity (%) | Density (g/ml) | Porosity (%) |
| PLLA/THF 5.0% | 0.0638 | 94.9 | 0.0587 | 95.3 | 0.0583 | 95.4 |
| PLLA/THF 7.5% | 0.0889 | 92.9 | 0.0885 | 93.8 | 0.0781 | 93.8 |
| PDLLA/(D/W)" 5.0% | 0.1996 | 84.0 | | | | |
| PLGA/(D/W)* 10% | 0.2359 | 81.1 | | | | |

TABLE 2

| | Gelation Time | | | |
|---|---|---|---|---|
| Gelation Temperature (° C.) | PLLA/THF 1.0% (wt/v) | PLLA/THF 2.5% (wt/v) | PLLA/THF 3.0% (wt/v) | PLLA/THF 5.0% (wt/v) |
| −18 | 15 min. | 12 min. | 10 min. | 8 min. |
| 8 | 150 min. | 40 min. | 30 min. | 25 min. |
| 15 | 24 hr. | 6 hr. | 4 hr. | 50 min |
| 23 | MG | MG | 12 hr. | 4 hr. |
| 30 | CS | MG | 24 hr. | 12 hr. |
| 35 | CS | CS | MG | 20 hr. |
| 40 | CS | CS | CS | MG |
| 45 | CS | CS | CS | CS |

TABLE 3

| Concentration (%) | Diameter (nm) | Porosity (%) | Unit Length (nm) | Surface/Volume Ratio ($\mu m^{-1}$) |
|---|---|---|---|---|
| 1.0 | 164 ± 71 | 98.5 | 2055 | 24.4 |
| 2.5 | 164 ± 90 | 97.4 | 1561 | 24.4 |
| 5.0 | 169 ± 74 | 95.3 | 1197 | 23.7 |
| 7.5 | 166 ± 74 | 93.8 | 1023 | 24.1 |

TABLE 4

| PLLA/THF concentration | Gelling temperature (° C.) | $T_m$ (° C.) | $\Delta H_m$ (J/g) | $X_c$ |
|---|---|---|---|---|
| 1.0% (wt/v) | −18 | 180.5 | 49.5 | 24.4 |
| 2.5% (wt/v) | −18 | 181.6 | 55.3 | 27.2 |
| 5.0% (wt/v) | −18 | 179.1 | 56.0 | 27.5 |
| 7.5% (wt/v) | −18 | 177.0 | 53.3 | 26.2 |
| 5.0% (wt/v) | liquid nitrogen | 180.7 | 56.8 | 27.9 |
| 5.0% (wt/v) | 8 | 183.4 | 53.2 | 26.2 |
| 5.0% (wt/v) | 15 | 180.2 | 57.6 | 28.3 |
| 5.0% (wt/v) | 23 | 182.5 | 74.2 | 36.5 |
| PLLA film | 23 | 179.3 | 68.2 | 33.5 |

We claim:

1. A method, comprising:

a) providing:
 i) a polymer preparation,
 ii) a solvent;

b) mixing said polymer with said solvent to create a polymer/solvent solution;

c) gelling said polymer/solvent solution; and d) treating said gelled polymer solution under conditions whereby a substantially solvent free fibrillar matrix is created having a porosity greater than approximately 80% wherein said fibrillar matrix comprises fibers having a diameter in the range of approximately 50 nm and 500 nm.

2. The method of claim 1, wherein said porosity is greater than approximately 85%.

3. The method of claim 1, wherein said porosity is greater than approximately 90%.

4. The method of claim 1, wherein said porosity is approximately 98%.

5. The method of claim 1, wherein said fibrillar matrix comprises fibers, wherein said fibers have a unit length between approximately 1000 nm and 2200 nm.

6. The method of claim 1, wherein said polymer preparation is selected from the group consisting of Poly(D,L-lactic acid) and Poly(L-lactic acid).

7. The method of claim 1, wherein said polymer preparation is a copolymer comprising poly(D,L-lactic acid-co-glycolic acid).

8. The method of claim 1, wherein said polymer preparation is comprised of a plurality polymers and copolymers selected from the group consisting of poly(L-lactic acid), Poly(D,L-lactic acid), and poly(D,L-lactic acid-co-glycolic acid).

9. The method of claim 1, wherein said solvent is selected from the group consisting of dioxane, tetrahydrofuran, N,N-dimethylformamide, pyridine, methanol and acetone.

10. The method of claim 1, wherein said solvent comprises a solution of dioxane and water.

11. The method of claim 1, wherein said polymer/solvent solution is contacted with compounds selected from the group consisting of salts, sugars, and water-soluble waxes.

12. A method, comprising:

a) providing:
 i) a polymer preparation,
 ii) a solvent b) mixing said polymer with said solvent to create a polymer solution;

c) gelling said polymer/solvent solution under conditions whereby a three-dimensional fibrillar matrix is created; and d) hydrating said gelled polymer/solvent solution maintained under conditions whereby a three-dimensional fibrillar network is preserved such that said gelled polymer/solvent solution maintained under conditions whereby said preserved fibrillar three-dimensional matrix is preserved is solvent free;

e) treating said hydrated solvent free gelled polymer three-dimensional fibrillar matrix under conditions whereby a solvent free fibrillar matrix is created having a porosity greater than approximately 80%.

13. The method of claim 12, wherein said porosity is greater than approximately 85%.

14. The method of claim 12, wherein said porosity is greater than approximately 90%.

15. The method of claim 12, wherein said porosity is approximately 98%.

16. The method of claim 12, wherein said fibrillar matrix comprises fibers having a diameter between approximately 50 nm and 500 nm.

17. The method of claim 12, wherein said fibrillar matrix comprises fibers, wherein said fibers have a unit length between approximately 1000 nm and 2200 nm.

18. The method of claim 12, wherein said polymer preparation is selected from the group consisting of Poly(D, L-lactic acid) and Poly(L-lactic acid).

19. The method of claim 12, wherein said polymer preparation is a copolymer comprising poly(D,L-lactic acid-co-glycolic acid).

20. The method of claim 12, wherein said polymer preparation is comprised of a plurality polymers and copolymers selected from the group consisting of poly(L-lactic acid), Poly(D,L-lactic acid), and poly(D,L-lactic acid-co-glycolic acid).

21. The method of claim 12, wherein said solvent is selected from the group consisting of dioxane, tetrahydrofuran, N,N-dimethylformamide, pyridine, methanol and acetone.

22. The method of claim 12, wherein said solvent comprises a solution of dioxane and water.

23. The method of claim 12, wherein said polymer/solvent solution is contacted with compounds selected from the group consisting of salts, sugars, and water-soluble waxes.

24. A method, comprising:
a) providing:
i) a polymer preparation,
ii) a solvent
b) mixing said polymer with said solvent to create a polymer solution;
c) casting said polymer/solvent solution into a desired form;
d) gelling said cast polymer/solvent solution under conditions whereby a three-dimensional fibrillar matrix is created;
e) hydrating said cast gelled polymer/solvent solution maintained under conditions whereby a three-dimensional fibrillar matrix is preserved such that said cast gelled polymer/solvent solution maintained under conditions whereby said preserved fibrillar three-dimensional matrix is solvent free; and
f) freezing said cast hydrated solvent-free three-dimensional matrix;
g) freeze-drying said cast hydrated solvent-free three-dimensional matrix such that a substantially desiccated fibrillar matrix is created having a porosity of greater than approximately 80%.

25. The method of claim 24, wherein said porosity is greater than approximately 85%.

26. The method of claim 24, wherein said porosity is greater than approximately 90%.

27. The method of claim 24, wherein said porosity is approximately 98%.

28. The method of claim 24, wherein said fibrillar matrix comprises fibers having a diameter between approximately 50 nm and 500 nm.

29. The method of claim 24, wherein said fibrillar matrix comprises fibers, wherein said fibers have a unit length between approximately 1000 nm and 2200 nm.

30. The method of claim 24, wherein said polymer preparation is selected from the group consisting of Poly(D, L-lactic acid) and Poly(L-lactic acid).

31. The method of claim 24, wherein said polymer preparation is a copolymer comprising poly(D,L-lactic acid-co-glycolic acid).

32. The method of claim 24, wherein said polymer preparation is comprised of a plurality polymers and copolymers selected from the group consisting of poly(L-lactic acid), Poly(D,L-lactic acid), and poly(D,L-lactic acid-co-glycolic acid).

33. The method of claim 24, wherein said solvent is selected from the group consisting of dioxane, tetrahydrofuran, N,N-dimethylformamide, pyridine, methanol and acetone.

34. The method of claim 24, wherein said solvent comprises a solution of dioxane and water.

35. The method of claim 24, wherein said polymer/solvent solution is contacted with compounds selected from the group consisting of salts, sugars, and water-soluble waxes.

36. A method, comprising:
a) providing:
i) a polymer preparation,
ii) a solvent
b) mixing said polymer with said solvent to create a polymer solution;
c) gelling said polymer/solvent solution at a temperature range between −195.8° C. to 23.0° C. such that a three-dimensional fibrillar matrix is created; and
d) hydrating said gelled polymer/solvent solution under conditions whereby said three-dimensional fibrillar matrix is preserved.

37. The method of claim 36, wherein said fibrillar matrix comprises fibers having a diameter between approximately 50 nm and 500 nm.

38. The method of claim 36, wherein said fibrillar matrix comprises fibers, wherein said fibers have a unit length between approximately 1000 nm and 2200 nm.

39. The method of claim 36, wherein said temperature range is between −18° C. and 8° C.

40. The method of claim 36, wherein said polymer preparation is selected from the group consisting of Poly(D, L-lactic acid) and Poly(L-lactic acid).

41. The method of claim 36, wherein said polymer preparation is a copolymer comprising poly(D,L-lactic acid-co-glycolic acid).

42. The method of claim 36, wherein said polymer preparation is comprised of a plurality polymers and copolymers selected from the group consisting of poly(L-lactic acid), Poly(D,L,-lactic acid), and poly(D,L-lactic acid-co-glycolic acid).

43. The method of claim 36, wherein said solvent is selected from the group consisting of dioxane, tetrahydrofuran, N,N-dimethylformamide, pyridine, methanol and acetone.

44. The method of claim 36, wherein said solvent comprises a solution of dioxane and water.

45. A method, comprising:
    a) providing:
        i) a polymer preparation,
        ii) a solvent
    b) mixing said polymer with said solvent to create a polymer solution;
    c) casting said polymer/solvent solution into a desired form;
    d) gelling said cast polymer/solvent solution at a temperature range between −195.8° C. to 23.0° C. such that a three-dimensional fibrillar matrix is created; and
    e) hydrating said cast gelled polymer/solvent solution maintained under conditions whereby a three-dimensional fibrillar matrix is preserved.

46. The method of claim 45, wherein said fibrillar matrix comprises fibers having a diameter between approximately 50 nm and 500 nm.

47. The method of claim 45, wherein said fibrillar matrix comprises fibers, wherein said fibers have a unit length between approximately 1000 nm and 2200 nm.

48. The method of claim 45, wherein said temperature range is between −18° C. and 8° C.

49. The method of claim 45, wherein said polymer preparation is selected from the group consisting of Poly(D, L-lactic acid) and Poly(L-lactic acid).

50. The method of claim 45, wherein said polymer preparation is a copolymer comprising poly(D,L-lactic acid-co-glycolic acid).

51. The method of claim 45, wherein said polymer preparation is comprised of a plurality polymers and copolymers selected from the group consisting of poly(L-lactic acid), Poly(D,L-lactic acid), and poly(D,L-lactic acid-co-glycolic acid).

52. The method of claim 45, wherein said solvent is selected from the group consisting of dioxane, tetrahydrofuran, N,N-dimethylformamide, pyridine, methanol and acetone.

53. The method of claim 45, wherein said solvent comprises a solution of dioxane and water.

54. A method, comprising:
    a) providing:
        i) a polymer preparation,
        ii) a solvent;
    b) mixing said polymer with said solvent to create a polymer/solvent solution;
    c) gelling said polymer/solvent solution; and
    d) treating said gelled polymer solution under conditions such that a substantially solvent free fibrillar matrix having a porosity greater than approximately 80% is created wherein said fibrillar matrix is comprised of fibers, said fibers having a unit length in the range of approximately 1000 nm and 2200 nm.

55. The method of claim 54, wherein said porosity is greater than approximately 85%.

56. The method of claim 54, wherein said porosity is greater than approximately 90%.

57. The method of claim 54, wherein said porosity is approximately 98%.

58. The method of claim 54, wherein said polymer preparation is selected from the group consisting of Poly(D, L-lactic acid) and Poly(L-lactic acid).

59. The method of claim 54, wherein said polymer preparation is a copolymer comprising poly(D,L-lactic acid-co-glycolic acid).

60. The method of claim 54, wherein said polymer preparation is comprised of a plurality polymers and copolymers selected from the group consisting of poly(L-lactic acid), Poly(D,L-lactic acid), and poly(D,L-lactic acid-co-glycolic acid).

61. The method of claim 54, wherein said solvent is selected from the group consisting of dioxane, tetrahydrofuran, N,N-dimethylformamide, pyridine, methanol and acetone.

62. The method of claim 54, wherein said solvent comprises a solution of dioxane and water.

63. The method of claim 54, wherein said polymer/solvent solution is contacted with compounds selected from the group consisting of salts, sugars, and water-soluble waxes.

* * * * *